United States Patent
Paul

(10) Patent No.: US 9,694,215 B2
(45) Date of Patent: Jul. 4, 2017

(54) SKIN COMPOSITIONS AND METHODS

(71) Applicant: Brian S. Paul, Los Angeles, CA (US)

(72) Inventor: Brian S. Paul, Los Angeles, CA (US)

( * ) Notice: Subject to any disclaimer, the term of this patent is extended or adjusted under 35 U.S.C. 154(b) by 0 days.

(21) Appl. No.: 14/550,322

(22) Filed: Nov. 21, 2014

(65) Prior Publication Data

US 2016/0143830 A1     May 26, 2016

(51) Int. Cl.

| | |
|---|---|
| *A61K 8/00* | (2006.01) |
| *A61Q 19/02* | (2006.01) |
| *A61K 8/02* | (2006.01) |
| *A61K 8/67* | (2006.01) |
| *A61Q 17/04* | (2006.01) |
| *A61Q 19/08* | (2006.01) |
| *A61Q 19/00* | (2006.01) |
| *A61K 8/34* | (2006.01) |
| *A61K 8/37* | (2006.01) |
| *A61K 8/60* | (2006.01) |
| *A61K 8/92* | (2006.01) |
| *A61K 8/97* | (2017.01) |

(52) U.S. Cl.
CPC ............ *A61Q 19/02* (2013.01); *A61K 8/0241* (2013.01); *A61K 8/34* (2013.01); *A61K 8/342* (2013.01); *A61K 8/345* (2013.01); *A61K 8/375* (2013.01); *A61K 8/602* (2013.01); *A61K 8/675* (2013.01); *A61K 8/676* (2013.01); *A61K 8/922* (2013.01); *A61K 8/97* (2013.01); *A61Q 17/04* (2013.01); *A61Q 19/007* (2013.01); *A61Q 19/08* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 2004/0081681 A1* | 4/2004 | Vromen | A61K 8/37 424/449 |
| 2013/0139841 A1 | 6/2013 | Dumousseaux et al. | |
| 2015/0118176 A1* | 4/2015 | Mendoza | A61K 8/8152 424/78.02 |

FOREIGN PATENT DOCUMENTS

WO     2013149323 A1     10/2013

OTHER PUBLICATIONS

International Search Report and Written Opinion; International Application No. PCT/US15/13903; International Filing Date Jan. 30, 2015; Date of Mailing Apr. 27, 2015; 6 pages.

* cited by examiner

*Primary Examiner* — Nannette Holloman
(74) *Attorney, Agent, or Firm* — Cantor Colburn LLP

(57) ABSTRACT

The invention provides skin compositions containing a mixture of milled particles having different sizes less than 50 microns in diameter of vitamins in a biocompatible carrier.

9 Claims, 1 Drawing Sheet

Von Luschan Skin Color Chart

SKIN COMPOSITIONS AND METHODS

FIELD OF THE INVENTION

The present invention relates to a cosmetic composition and in particular to a skin conditioning composition.

BACKGROUND OF TOE INVENTION

It is known that ultra-violet radiation from the sun can cause acute adverse effects such as premature aging of skin and discoloration. Over a period of years, skin exposed to the sun may become permanently darker than the other unexposed skin, sun spots and areas of hyper pigmentation may also occur. A "tan" is essentially the skin's way of increasing its defense against the onslaught of damaging ultra-violet light. Tanning protects against sun damage principally by Increasing the melanin content of the epidermis. It is well known that light radiation of wavelengths of from 280 nm to 400 nm promotes tanning of the human epidermis, and that irradiation of wavelengths of from 280 to 320 nm. i.e., UV-B, causes erythema and burning of the skin. Melanin which is basically responsible for skin pigmentation is synthesized by melanocytes, a cell type present at dermis-epidermis junction, from an amino acid tyrosine. Tyrosine is acted upon by an enzyme tyrosinase which is the key enzyme in melanogenesis, free radicals are necessary for this reaction, however free radicals can cause skin cell damage.

Conventional skin lightening compositions are based on sunscreens which maintain skin color against ultra-violet light. They have been based on materials which absorb/block incident ultra-violet light of the wavelength which produces the tanning of the skin. Sunscreens alone cannot lighten the skin significantly and their action on the skin is only to reduce the ingress of incident ultra-violet into the skin and is therefore effective only during the day. Other approaches have been to use skin lightening agents which are believed to control dispersion of melanosomes or inhibit tyrosinase.

Sebum is produced in the skin adds a protective oil layer that protects the skin and contributes to the retention of moisture in the skin. It provides a natural glow and sheen to the skin. Modern cleansing with detergents removes the natural oil layer on the skin.

Patent GB 1 533 1 19 discloses cosmetic composition having a combination of niacinamide and a mixture of UV absorbers, which absorb in the UV range of 290 nm to 360 nm. IN 169917 discloses the use of a silicone compound to synergistically enhance skin lightening benefits obtained from the combination of niacinamide and sunscreens. Patent IN 172889 discloses the use of titanium dioxide at levels from 3% along with octyl methoxy cinnamate to provide protection from excessive exposure to ultra-violet fays over a broad range of wavelengths in the UV-A and UV-B regions. U.S. Pat. Nos. 5,997,887 and 5,997,890 disclose topical compositions comprising pigmentary grade particulate material such as titanium dioxide, with a particle size greater than 100 nm to about 300 nm along with an active vitamin $B_3$ useful for imparting an essentially immediate visual improvement in skin appearance. Vitamin C has been shown to help with skin damage resulting from exposure to the sun. (Farris, P K, Dermatol. Surg. 2005 July; 31(7 Pt 2):814-7).

Kojic acid has also been described to lighten skin and reduce tanning. (U.S. Pat. No. 4,278,656). Astaxanthin due to its antioxidant properties may also protect skin and provide desired coloration. (H. Corrales Padilla, et al., Int. J. Dermatol. 13(5):276-282 (1974); D. Jimenez, et al. Allergol. et Immunopathol. 15(4):185-189 (1987)).

The stratum corneum of skin poses a barrier to transmission of active ingredients of topical compositions into the layers of the skin. Milled particles, i.e. particles of less than 500 nm of different sizes, have been shown to penetrate layers of the skin for topical compositions. (Dermatoendocrinol. 2009 July-August; 1(4): 197-206). A possible route for entry of topically applied agents is through microchannels between the cells of the stratus corneum. (Verma and Fahr, Eur. J. Pharm. Biopharm 2003:55:271-277).

Despite the development of skin compositions, there is an ongoing need to provide effective and safe compositions for conditioning and improving the appearance of skin.

SUMMARY OF THE INVENTION

Accordingly, the compositions of the invention provide skin compositions comprising a mixture of milled particles of different sizes having a diameter less than 50 microns of of niacin and vitamin C. The composition may be included in a suitable carrier, that may be one or more of propylene glycol diperlargonate (DPPG), castor oil, sunflower, coconut oil, shea butter, cetyl alcohol, caprylic triglyceride, lanolin and bees wax. The milled particles may be less than 10 microns in diameter. The vitamin C may be magnesium L-ascorbate, magnesium ascorbyl phosphate, or L-ascorbylpalmitate. The skin composition may include vitamin B, vitamin D, vitamin E, vitamin A and mixtures thereof, and may include an agent providing protection from ultraviolet radiation.

The skin composition may be a mixture of milled particles having different sizes and a diameter less than 50 microns of niacin and vitamin C and a suitable carrier.

The skin composition comprising a mixture of milled particles of different sizes and having a diameter less than 50 microns of niacin and Vitamin C in a mixture of water, caprylic/capric triglyceride, cetearyl alcohol glycerin, cetearyl glycoside, phenoxyethanol, coconut oil, shea butter, aloe vera extract, chamomile and green tea.

The invention also includes a method for improving the condition and appearance of skin by applying a composition comprising milled particles having a diameter of from approximately 0.1 to approximately 50 microns of vitamin C and niacin in a suitable carrier to the skin of a subject. The method where the skin composition may further include an agent providing protection from ultraviolet radiation.

In an embodiment, the skin compositions may have a mixture of milled particles having a diameter less than 50 microns of a mixture of niacin and vitamin C and a suitable carrier.

In another embodiment, the skin compositions have a mixture of milled particles having a diameter less than 50 microns of a mixture of water, caprylic/capric triglyceride, cetearyl alcohol glycerin, cetearyl glucoside, phenoxyethanol, coconut oil, shea butter, aloe vera extract, chamomile and green tea.

The invention further includes a method for improving the condition and appearance of skin comprising applying a composition comprising a mixture of milled particles having a diameter of from approximately 0.01 microns to approximately 50 microns of a mixture of a vitamin C and niacin in a suitable carrier. In the method, the composition may include an agent providing protection from ultraviolet radiation.

BRIEF DESCRIPTION OF THE DRAWING

FIG. 1 is a Von Luschan Skin Color Chart of skin color shades recorded before and after the trial in Example 1.

DETAILED DESCRIPTION

The skin compositions of the invention provide bioactive agents, such as vitamins, in the form of a mixture of milled panicles of less than 50 microns in diameter which may be added to a suitable carrier for improving the condition and appearance of the skin. For example, the compositions may be used on human facial skin, for example, to lighten dark spots, while moisturizing and otherwise conditioning and improving the appearance of skin Suitable ingredients for use in the skin compositions include, but are not limited to forms of niacin and forms of vitamin C. The niacin may be in the form of nicotinic acid esters, non-vasodilating esters of nicotinic acid, vitamin B3. nicotinyl amino acids, nicotinyl alcohol esters of carboxylic acids, nicotinic acid N-oxide. niacin amide N-oxide and mixtures thereof. Vitamin C may be provided as magnesium aceorbate, magnesium ascorbyl phosphate, magnesium L-ascorbate or L-ascorbyl palmitate. Additional vitamins may be added, such as vitamins B6, D3, E and A.

While not wishing to be bound by any particular theory, the antioxidant properties of the skin composition of the invention reduce free radicals engaged in skin damage and the various cascades that are involved in the pigmentation of the skin, specifically related but not limited to stem cell factor and endothelin-1, and inflammation from mast cells. In addition, the vitamin C in the compositions is involved in collagen synthesis and may aid in skin repair.

The mixed milled particle composition may be formulated as a dry powder and added to the biocompatible carrier which may be oil based or a lipid and water emulsion, and may dissolve the skin composition bioactive ingredients, such as the vitamins, retaining a portion of the bioactive ingredients within layers of the skin by resisting removal from events such as cleansing the skin. Suitable carriers include, but are not limited to, propylene glycol diperlargonate (DPPG), cetyl alcohol, esters, castor oil, shea butter, neem oil paraffin oils, lanolin and its derivatives, sunflower oil, coconut oil, cetyl alcohol, caprylic triglyceride, or bees wax and mixtures thereof. The suitable carrier may be from approximately 5% to approximately 95% by weight of the total weight after the dry mixed milled particle composition of the invention has been added to the carrier.

In addition, the skin compositions may include, powder absorbents, binders, and liquids such as emollients, emulsifiers, propellants, solvents, humectants (e.g polyols, glycerol), thickeners (e.g. Carbopol 934), and skin lighteners such as licorice extract, fragrances and colorants, such as astaxanthin. Other ingredients known to promote skin health and appearance, for example, green tea, chamomile and the like, may be added to the compositions of the invention. The skin composition may include vitamin B, vitamin D, vitamin E, vitamin A, Ashwaganda (contains Withaferin A), M. Chamomilla extract, Melia Toosendan extract and mixtures thereof.

In addition, ultraviolet protectants and/or blockers, such as titanium oxide, may be added to the skin compositions.

The mixed milled particles of the skin compositions include a mixture of sizes of particles within the range of from 0.1 microns to 50 microns in diameter. The larger particles may assist in exfoliation of the outer layers of the skin during application of the composition to the skin, permitting better access of the bioactive ingredients, such as vitamins, into the skin, and the smaller particles may more readily penetrate deeper into the layers of the skin.

The mixed milled particles of the skin composition, and may be from approximately 0.1% to approximately 25%, or from approximately 0.1% to approximately 15%, by weight of the composition, plus suitable carrier.

The skin compositions may be added to existing skin compositions, for example cleansing or moisturizing creams and oils, and to those containing sunscreens and other active agents, such as antioxidants, to improve the appearance of the skin.

In the method of the invention, the skin compositions in the suitable oil based carrier may be applied topically to the skin, for example the skin of the human face, to improve the appearance of the skin by moisturizing and lightening areas of the skin. The compositions may be applied after cleansing, one or more times a day, for example by applying a pea-sized amount of composition and spreading liberally to areas of the skin that appear to require extra care.

The skin compositions for topical application to the skin can be in the form of conventional topical skin compositions, including lotions, powders, creams, ointments, sticks or atomized, for example in aerosol sprays or pumps.

While not wishing to be bound by any theory, the skin compositions that contain mixed milled particles of bioactive agents improve penetration and retention of the bioactive agents within the skin, thereby reducing moisture loss from the skin and improving the appearance of the skin, including by moisturizing and lightening the skin. The skin compositions ingredients may also contain photoprotective properties to the skin, and can be used in conjunction with protection against ultraviolet light as well as provide antioxidant benefits.

The invention will now be illustrated by way of an example. The example is for illustration only and does not in any way restrict the scope of the invention.

EXAMPLE I

One gram (g) of a composition containing a mixture of milled particles of less than 50 microns in diameter, prepared by jet milling 0.5 g of vitamin C (magnesium L aceorbate) and 0.5 and 0.5 g of niacin (nicotinic acid) were prepared. Particle sizes of from approximately 0.5 to approximately 31 microns were contained in the mixture as determined by Microtrac instrument analysis. (Microtrac. Inc., York, Pa. 17404). This mixture was blended with 10 grams of an emulsion base cream (GAR labs, Inland Empire Calif.). The composition was placed in an airless pump to reduce degradation, or mixed and used within a few days of testing. The composition was applied twice dally to the cheek, forehead and under the eyes of the face, and to calluses on the toes of the feet and elbows, of the arms of six volunteer human subjects. The various mapped areas of the subjects' skin receiving the composition and those skin areas not receiving composition (controls), had their skin color shades recorded before and after the trial, using the von Luschan chart (Indian Journal of Dermatology 2014 July August 59(4) 339-342). Measurements were taken again after two weeks of use, and every two weeks, for the six week duration of the trial. The composition was applied twice daily, after the subjects washed their faces and bodies, inthe morning and at night before bed. To compare overall change, as well as changes in the condition of skin in specific areas each area received an average-aggregate score using the Von Luschan chart. The score for each subject was added and then divided by the number of subjects. Only the scores for like areas were added. The data is shown in FIG. 1.

The test human subjects and the expert panel members were also asked to score the brightness of the skin and glow on the skin, immediately after application of the cream, and also after the composition had completely dried on the skin. The percentage of test subjects stating that composition of example 3, "makes my skin bright" was 100% and "makes my skin glow" was 100%.

TABLE 1

Aggregate Von Luschan Chart Score of Subjects after Application of Composition

| | Subject # (1-6 weeks) | | | | | |
|---|---|---|---|---|---|---|
| | Aggregate Average score, treated area, start | Aggregate score treated area, 2 weeks | Aggregate score treated area, 4 weeks | Aggregate score treated area, 6 weeks | Improvement in skin quality, moisture and feel, glow | Fine lines and wrinkles dryness |
| Face cheek | 29 | | 26 | 24 | Yes | Yes |
| Toe callus | 35 | | 29 | 28 | Yes | Yes |
| Eye circle | 35 | | 33 | 29 | Yes | Yes |
| forehead | 30 | | 26 | 24 | Yes | Yes |

The description of the different illustrative embodiments has been presented for purposes of illustration and description, and is not intended to be exhaustive or limited to the embodiments in the form disclosed. It is understood that various changes can be made In the ingredients of the compositions and methods without departing from the scope defined by the claims.

I claim:

1. A skin composition, the composition comprising a mixture of milled particles having different size diameters between 0.1 and 50 microns, the particles comprising a mixture of niacin and magnesium ascorbate, wherein the particles are suspended in an oil and water based biocompatible carrier,
   wherein the larger diameter particles assist in exfoliation of the outer layers of the skin during application of the composition, and the smaller diameter particles penetrate into the skin.

2. The composition of claim 1, wherein the oil is propylene glycol diperlargonate (DPPG), castor oil, sunflower, coconut oil, shea butter, cetyl alcohol, caprylic triglyceride, lanolin, bees wax, or a mixture thereof.

3. The skin composition of claim 1, wherein said milled particles are less than 10 microns in diameter.

4. The skin composition of claim 1, further comprising vitamin B, vitamin D, vitamin E, vitamin A, or a mixture thereof.

5. The skin composition of claim 1, further comprising an agent providing protection from ultraviolet radiation.

6. A skin composition comprising a mixture of milled particles of different sizes and having a diameter between 0.1 and 50 microns, the particles comprising a mixture of niacin and magnesium ascorbate in a mixture of water, caprylic/capric triglyceride, cetearyl alcohol, glycerin, cetearyl glucoside, phenoxyethanol, coconut oil, sheabutter, aloe vera extract, chamomile and green tea,
   wherein the larger diameter particles assist in exfoliation of the outer layers of the skin during application of the composition, and the smaller diameter particles penetrate into the skin.

7. A method for improving the condition and appearance of skin, comprising
   applying to the skin of a subject a composition comprising milled particles having a diameter of 0.1 to 50 microns, the particles comprising a mixture of magnesium ascorbate and niacin, wherein the particles are in an oil and water based biocompatible carrier,
   wherein the larger diameter particles assist in exfoliation of the outer layers of the skin during application of the composition, and the smaller diameter particles penetrate into the skin.

8. The method of claim 7, wherein the composition further comprises an agent providing protection from ultraviolet radiation.

9. The method of claim 8, wherein the composition further comprises vitamin B, vitamin D, vitamin E, vitamin A, or a mixture thereof.

* * * * *